United States Patent [19]

Takamura et al.

[11] Patent Number: 4,973,600
[45] Date of Patent: Nov. 27, 1990

[54] BENZODIOXOLE DERIVATIVES, PHARMACEUTICAL COMPOSITIONS AND USE

[75] Inventors: Norio Takamura, Asaka; Isao Inoue, Toda; Masaru Inage, Kitamoto; Isao Yamaguchi, Suginami, all of Japan

[73] Assignee: Tanabe Seiyaku Co., Ltd., Osaka, Japan

[21] Appl. No.: 304,252

[22] Filed: Jan. 31, 1989

[30] Foreign Application Priority Data

Feb. 16, 1988 [JP] Japan .................................. 63-33693

[51] Int. Cl.$^5$ .................. A61K 31/415; C07D 405/06
[52] U.S. Cl. .................................... 514/406; 546/270; 548/374; 514/869
[58] Field of Search ........................ 546/270; 548/374; 514/338, 406, 869

[56] References Cited

U.S. PATENT DOCUMENTS 4,517,184  5/1985  Habicht et al. ...................... 548/374

Primary Examiner—Robert W. Ramsuer
Attorney, Agent, or Firm—Browdy and Neimark

[57] ABSTRACT

Novel benzodioxole derivative of the formula:

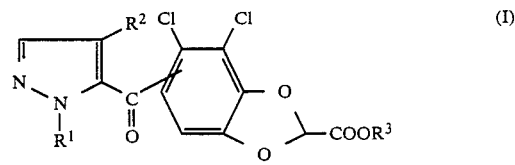

wherein $R^1$ is a lower alkyl group, a lower alkoxy-lower alkyl group, phenyl group or pyridyl group, $R^2$ is hydrogen atom or a halogen atom and $R^3$ is hydrogen atom or a lower alkyl group, and a salt thereof are disclosed.

Said derivative (I) and a salt thereof have potent diuretic, saluretic and uricosuric activities.

9 Claims, No Drawings

BENZODIOXOLE DERIVATIVES, PHARMACEUTICAL COMPOSITIONS AND USE

FIELD OF THE INVENTION

This invention relates to a benzodioxole derivative and processes for preparing the same. More particularly, it relates to a benzodioxole derivative of the formula:

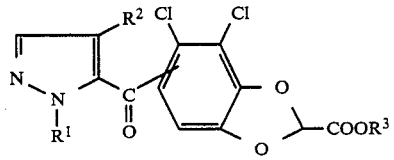

wherein $R^1$ is a lower alkyl group, a lower alkoxy-lower alkyl group, phenyl group or pyridyl group, $R^2$ is hydrogen atom or a halogen atom and $R^3$ is hydrogen atom or a lower alkyl group, or a salt thereof.

BACKGROUND OF THE INVENTION

Known diuretic agents include thiazide diuretics such as chlorothiazide or hydrochlorothiazide and loop diuretics such as furosemide or ethacrynic acid. These agents are useful to increase urine volume and electrolyte excretion by inhibiting reabsorption of water and electrolytes from renal tubules. However, these known diuretics are not satisfactory in that they are liable to cause hyperuricemia which often results in interstitial nephritis or gout due to deposition of uric acid in tissue of living body. Therefore, there has been need to develop diuretics which can promote excretion of not only water and electrolytes but also uric acid. On the other hand, U.S. Pat. No. 4,517,184 disclose benzodioxole derivatives such as 5-benzoyl-6-chloro-1,3-benzodioxole-2-carboxylic acid, 5-methyl-6-nicotinoyl-1,3-benzodioxole-2-carboxylic acid and the like which are useful as a diuretic agent.

SUMMARY OF THE INVENTION

We have now found that the benzodioxole derivatives (I) and its salts have potent diuretic, saluretic and uricosuric activities. For example, when the effect of a test compound on urine volume was examined by administering a carboxymethylcellulose solution thereof (dose: 30 mg/kg) orally to saline-loaded rats, each one of 4,5-dichloro-6-(1-methyl-5-pyrazolylcarbonyl)-1,3-benzodioxole-2-carboxylic acid, 4,5-dichloro-6-(1-ethyl-5-pyrazolylcarbonyl)-1,3-benzodioxole-2-carboxylic acid, 4,5-dichloro-6-(1-propyl-5-pyrazolylcarbonyl)-1,3-benzodioxole-2-carboxylic acid and 4,5-dichloro-6-(1-methoxymethyl-5-pyrazolylcarbonyl)-1,3-benzodioxole-2-carboxylic acid showed more than 100% increase in the urine volume as compared with a control group of rats.

Moreover, for example, when the effect of a test compound on uric acid excretion was examined by administering a carboxymethylcellulose solution thereof (dose: 100 mg/kg) orally to saline-loaded rats, each one of 4,5-dichloro-6-(1-ethyl-5-pyrazolylcarbonyl)-1,3-benzodioxole-2-carboxylic acid, 4,5-dichloro-6-(1-propyl-5-pyrazolylcarbonyl)-1,3-benzodioxole-2-carboxylic acid and 4,5-dichloro-6-(1-methyl-4-chloro-5-pyrazolylcarbonyl)-1,3-benzodioxole-2-carboxylic acid showed more than 50% increase in the uric acid excretion as compared with a control group of rats.

Examples of the compound of the present invention include those of the formula (I) in which $R^1$ is a $C_{1-6}$alkyl group (e.g., methyl group, ethyl group, n-propyl group, isopropyl group, butyl group, pentyl group, hexyl group), a $C_{1-4}$alkoxy-$C_{1-4}$alkyl group (e.g., methoxymethyl group, methoxyethyl group, ethoxymethyl group), phenyl group or pyridyl group, $R^2$ is hydrogen atom or a halogen atom (e.g., chlorine atom, bromine atom, iodine atom) and $R^3$ is hydrogen atom or a $C_{1-4}$alkyl group (e.g., methyl group, ethyl group, n-propyl group, isopropyl group).

Among these compounds of the present invention, preferred examples of the compound include those of the formula (I) in which $R^1$ is a $C_{1-4}$alkyl group or a $C_{1-4}$alkoxy-$C_{1-4}$alkyl group, $R^2$ is hydrogen atom or chlorine atom, $R^3$ is hydrogen atom or a $C_{1-4}$alkyl group.

More preferred examples of the compound include those of the formula (I) in which $R^1$ is methyl group, ethyl group, n-propyl group, isopropyl group, methoxymethyl group or ethoxymethyl group, $R^2$ is hydrogen atom or chlorine atom, $R^3$ is hydrogen atom or ethyl group and the 1-substituted-5-pyrazolylcarbonyl group is at 6-position of the benzodioxole skeleton.

Further preferred examples of the compound of the peresnt invention are those of the formula (I) in which $R^1$ is methyl group, ethyl group, n-propyl group or methoxymethyl group, $R^2$ is hydrogen atom or chlorine atom, $R^3$ is hydrogen atom and the 1-substituted-5-pyrazolylcarbonyl group is at 6-position of the benzodioxole skeleton.

According to the present invention, the benzodioxole derivative (I) or a salt thereof can be prepared by the step A-(i) reacting a 1,2-benzenediol compound of the formula:

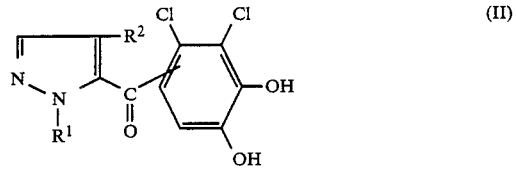

wherein $R^1$ and $R^2$ are the same as defined above, with an acetic acid compound of the formula:

$$(Y)_2CHCOOR^3 \qquad (III)$$

wherein Y is a reactive residue and $R^3$ is the same as defined above, to give the compound (I); or -(ii) oxidizing a compound of the formula:

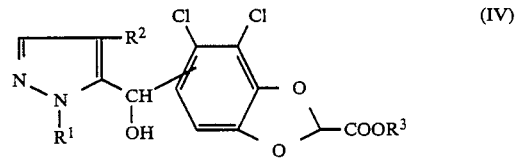

wherein $R^1$, $R^2$ and $R^3$ are the same as defined above, to give the compound (I); or -(iii) hydrolysing a compound of the formula:

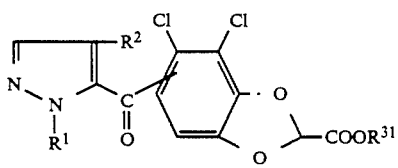

wherein $R^{31}$ is a lower alkyl group, and $R^1$ and $R^2$ are the same as defined above, to give a compound of the formula:

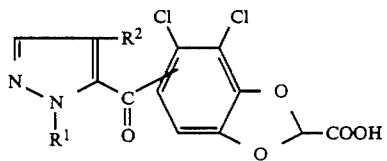

wherein $R^1$ and $R^2$ are the same as defined above; or

-(iv) halogenating a compound of the formula:

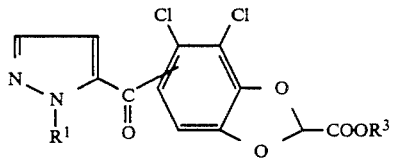

wherein $R^1$ and $R^3$ are the same as defined above, to give a compound of the formula:

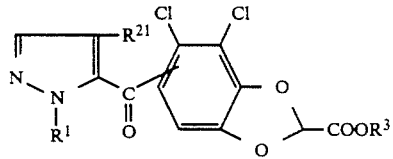

wherein $R^{21}$ is a halogen atom, and $R^1$ and $R^3$ are the same as defined above; and (B) if required, further converting the product into a salt thereof.

Examples of the reactive residue Y in the starting compound (III) include a halogen atom such as chlorine, bromine or iodine, tosyloxy and methanesulfonyloxy.

The reaction of the 1,2-benzenediol compound (II) with the acetic acid compound (III) can be carried out in a solvent in the presence of an acid acceptor. The acid acceptor includes, for example, alkali metal hydroxides such as sodium hydroxide or potassium hydroxide, alkaline earth metal hydroxides such as calcium hydroxide or barium hydroxide, alkali metal carbonates such as sodium carbonate or potassium carbonate, alkali metal bicarbonates such as sodium bicarbonate or potassium bicarbonate, alkali metal hydrides such as sodium hydride or potassium hydride, alkali metal lower alkoxides such as sodium ethoxide or potassium t-butoxide, lithium diisopropylamide, sodium amide, lithium amide, alkali metal fluorides such as potassium fluoride or cesium fluoride, and an organic bases such as triethylamine or tributylamine. Lower alkanones such as acetone or methylethylketone, lower alkanols such as methanol or ethanol, tetrahydrofuran, dioxane, dimethylformamide, dimethylsulfoxide or a mixture of water and the afore-mentioned organic solvent is preferably used as the solvent. It is preferred to carry out the reaction at a temperature of 0° to 100° C., especially 20° to 80° C.

The oxidation of the compound (IV) can be carried out by treatment with an oxidizing agent in a solvent. Methylene chloride, chloroform, lower alkanones such as acetone or methylethylketone, benzene, toluene, hexane, petroleum ether, acetonitrile, dimethylformamide, dimethylsulfoxide, acetic acid, tetrahydrofuran, dioxane or a mixture of water and the afore-mentioned organic solvent is preferably used as the solvent. Suitable examples of the oxidizing agent include manganese dioxide, chromic acid anhydride, potassium permanganate, acetic anhydride-dimethylsulfoxide, chloranil, 2,3-dichloro-5,6-dicyanobenzoquinone and dinitrogen tetraoxide. It is preferred to carry out the reaction at a temperature of −78° to 100° C., especially 0° to 50° C.

The hydrolysis of the benzodioxole compound (I-A) can be carried out by treating said compound with an acid or a base in a solvent. Examples of the acid include mineral acids such as hydrochloric acid, hydrobromic acid or sulfuric acid, and examples of the base include alkali metal hydroxides such as sodium hydroxide or potassium hydroxide, and alkaline earth metal hydroxides such as barium hydroxide. Lower alkanols such as methanol or ethanol, tetrahydrofuran, dioxane, dimethylformamide, dimethylsulfoxide, water or a mixture thereof is preferably used as the solvent. It is preferred to carry out the reaction at a temperature of 0° to 100° C., especially at 20° to 100° C. in case the acid is used, or at 0° to 60° C. in case the base is used.

The halogenation of the compound (I-C) can be carried out by reacting said compound with a halogenating agent in a solvent. Examples of the halogenating agent include chlorine, bromine, iodine, sulfuryl halide such as sulfuryl chloride, phosphorus pentachloride, N-halogenosuccinimide such as N-chlorosuccinimide or N-bromosuccinimide, alkali metal bromite such as sodium bromite or alkali metal hypochlorite such as sodium hypochlorite. Acetic acid, dimethylformamide, methylene chloride, chloroform, dichloroethane, water or a mixture thereof is suitable as the solvent. It is preferred to carry out the reaction at a temperature of −20° to 100° C., especially 0° to 60° C.

The thus-obtained compound (I) of the present invention can be converted into a salt thereof in a traditional manner, for example, by reacting said compound with a substantially equimolar amount of an acid or a base in a solvent.

As mentioned hereinbefore, the benzodioxole derivatives (I) of the present invention and salts thereof show potent diuretic, saluretic and uricosuric activities, and are useful for treatment and/or prophylaxis of congestive heart failure, a wide variety of edema (e.g., hepatic edema, nephrotic edema, cardiac edema, hydrops gravidarum (=edema of pregnancy), lymphatic edema, drug-induced edema, pulmonary edema), hydrops ascites, exudative pleurisy, interstitial nephritis, gout or hyperuricemia.

The compound (I) of the present invention can be used for pharmaceutical use either in the free form or in the form of a salt thereof. Examples of the salt of the compound (I) include alkali metal salts such as sodium salt or potassium salt, alkaline earth metal salts such as calcium salt, inorganic acid addition salts such as hydrochloride, hydrobromide and sulfate, organic acid addition salts such as oxalate, methanesulfonate and the like.

The compound (I) or a salt thereof can be administered either orally or parenterally. For oral administration, the compound (I) and a salt thereof may be used in the solid form such as tablets, powders, capsules or granules, which may contain conventional carriers, binders, diluents, disintegrators, wetting agents and the like. They may also be used in liquid form such as suspensions, solutions, syrups or elixires. On the other hand, for parenteral administration, the compound (I) or a salt thereof may be used, for example, in the form of injections.

The dose of the compound (I) or a salt thereof may vary over a wide range depending on the administration route, the age, body weight or conditions of patients and the kind and severity of diseases to be treated. In general, however, preferred daily dose of the compound (I) or a salt thereof is in the range of 0.1 to 200 mg/kg/day, especially 0.3 to 100 mg/kg/day.

Concomitantly, the starting compound (II) may be prepared by treating a compound of the formula:

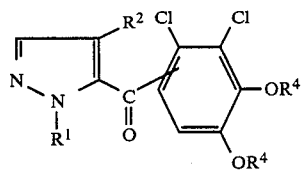
(VI)

wherein $R^4$ is a lower alkyl group, and $R^1$ and $R^2$ are the same as defined above, with hydrobromic acid, an alkali metal cyanide, an alkali metal thiolacetate, boron tribromide and the like.

On the other hand, the compound (IV) may be prepared by treating a compound of the formula:

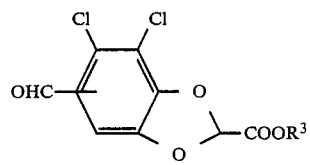
(VII)

wherein $R^3$ is the same as defined above with a compound of the formula:

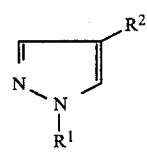
(VIII)

wherein $R^1$ and $R^2$ are the same as defined above, or by treating a compound of the formula:

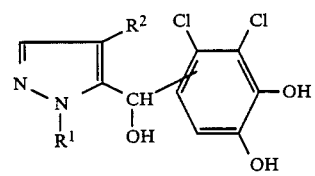
(IX)

wherein $R^1$ and $R^2$ are the same as defined above with the acetic acid compound (III).

The present invention will be illustrated by the following examples of methods of preparing the new compounds according to the invention.

DETAILED DESCRIPTION OF THE INVENTION

EXAMPLE 1

(1) A mixture of 6.25 g of (1-methylpyrazol-5-yl)-(2,3-dichloro-4,5-dimethoxyphenyl)-methanone and 70 ml of aqueous 47% hydrobromic acid is refluxed for 3 hours and the reaction mixture is evaporated to remove solvent. The residue is dissolved in aqueous 10% sodium hydroxide solution and the solution is adjusted to pH 3–4 by addition of acetic acid. The mixture is extracted with ethyl acetate. The extract is washed with an aqueous saturated sodium chloride solution, dried and evaporated to remove solvent under reduced pressure. The residue is crystalized from isopropyl ether and the crystals are collected by filtration to give 4.77 g of (1-methylpyrazol-5-yl)-(2,3-dichloro-4,5-dihydroxyphenyl)-methanone. Yield: 84% m. p. 202°–204° C.

(2) To a solution of 2.0 g of (1-methylpyrazol-5-yl)-(2,3-dichloro-4,5-dihydroxyphenyl)-methanone in 22 ml of dimethylformamide are added 2.12 g of powdered potassium carbonate and 3.7 g of ethyl dibromoacetate, and the mixture is stirred at 90° to 100° C. under argon gas atmosphere for 2 hours. After cooling, the mixture is poured into ice-water and the mixture is extracted with ethyl acetate. The extract is washed with an aqueous saturated sodium chloride solution, dried and evaporated to remove solvent under reduced pressure. The residue is purified by silica gel column chromatography (solvent; n-hexane-ethyl acetate) to give 1.64 g of ethyl 4,5-dichloro-6-(1-methyl-5-pyrazolylcarbonyl)-1,3-benzodioxole-2-carboxylate. Yield: 63% m. p. 124°–126.5° C. IR$\nu$(Nujol)cm$^{-1}$: 1760, 1660

EXAMPLES 2 to 9

(1) The corresponding starting compounds are treated in the same manner as described in Example 1-(1) to give the compounds as shown in following Table 1.

TABLE 1

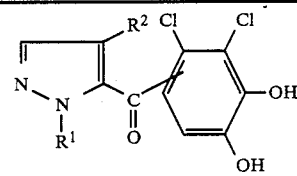
(II-a)

| Compound (II-a) | | | |
|---|---|---|---|
| $R^1$ | $R^2$ | *Position | Properties |
| CH$_3$— | H | 6 | Yield: 85% m.p. 227–230° C. (decomp.) |
| **CH$_3$— | Cl | 5 | Yield: 98% m.p. 211–213° C. (decomp.) |
| CH$_3$CH$_2$— | H | " | Yield: 75% m.p. 175.5–177.5° C. |
| CH$_3$CH$_2$CH$_2$— | " | " | Yield: 59% m.p. 172.5–175.5° C. |
| (CH$_3$)$_2$CH— | " | " | Yield: 77% m.p. 186.5–189° C. |
| CH$_3$(CH$_2$)$_5$— | " | " | Yield: 65% m.p. 146–147.5° C. |

TABLE 1-continued

Structure (II-a): pyrazole with R², Cl substituents, connected via C=O to dichlorobenzenediol with two OH groups, N-R¹

| R¹ | R² | *Position | Properties |
|---|---|---|---|
| phenyl | " | " | Yield: 85%<br>m.p. 167–169° C. |
| **pyridyl | " | " | This product was used in the next step immediately after crystallization from ether. |

Notes;
*Position means the position of the 1-substituted pyrazol-5-carbonyl group which is substituted on 3,4-dichloro-1,2-benzenediol compound.
**These compounds are prepared by dealkylation of the corresponding 1,2-dimethoxybenzene compounds with boron tribromide.

(2) The following compounds are obtained from the compounds as shown in table 1 in the same manner as described in Example 1-(2).

TABLE 2

Compound (I-a): pyrazole with R², Cl; C=O link to dichloro-benzodioxole with COOCH₂CH₃

| Example Nos. | R¹ | R² | *Position | Properties |
|---|---|---|---|---|
| 2 | $CH_3-$ | H | 7 | Yield: 53%<br>m.p. 95–97° C.<br>IR$\nu$(Nujol)cm$^{-1}$: 1740, 1650<br>MS(m/e): 370(M$^+$) |
| 3 | " | Cl | 6 | Yield: 52%<br>IR$\nu$(liquid)cm$^{-1}$: 1760, 1660<br>MS(m/e): 404(M$^+$) |
| 4 | $CH_3CH_2-$ | H | " | Yield: 54%<br>m.p. 108–111° C.<br>IR$\nu$(Nujol)cm$^{-1}$: 1760, 1650<br>MS(m/e): 384(M$^+$) |
| 5 | $CH_3CH_2CH_2-$ | " | " | Yield: 56%<br>IR$\nu$(liquid)cm$^{-1}$: 1750, 1660<br>MS(m/e): 39(M$^+$) |
| 6 | $(CH_3)_2CH-$ | " | " | Yield: 60%<br>m.p. 97.5–99° C.<br>IR$\nu$(Nujol)cm$^{-1}$: 1760, 1660<br>MS(m/e): 398(M$^+$) |
| 7 | $CH_3(CH_2)_5-$ | " | " | Yield: 73%<br>IR$\nu$(liquid)cm$^{-1}$: 1760, 1660<br>MS(m/e): 440(M$^+$) |
| 8 | phenyl | " | " | Yield: 60%<br>m.p. 119–120.5° C.<br>IR$\nu$(Nujol)cm$^{-1}$: 1760, 1660<br>MS(m/e): 432(M$^+$) |
| 9 | pyridyl | " | " | Yield: 54%<br>m.p. 147–149° C.<br>IR$\nu$(Nujol)cm$^{-1}$: 1760, 1660<br>MS(m/e): 398(M$^+$-Cl) |

Note;
*Position means the position of the 1-substituted pyrazole-5-carbonyl group which is substituted on the benzodioxole skeleton.

EXAMPLE 10

6.9 g of potassium carbonate and 2.83 g of dibromoacetic acid are added to a solution of 3.01 g of (1-ethyl-pyrazol-5-yl)-(2,3-dichloro-4,5-dihydroxyphenyl)-methanone in 30 ml of dimethylformamide and the mixture is stirred at 80° C. for 5 hours. After cooling the reaction mixture, water is added thereto and the mixture is adjusted to pH 1 by addition of 6N hydrochloric acid. The resultant crystals are collected by filtration, washed with water and recrystallized from dimethylformamide-water to give 1.36 g of 4,5-dichloro-6-(1-ethyl-5-pyrazolylcarbonyl)-1,3-benzodioxole-2-carboxylic acid.

m. p. 233°–235° C. (decomp.)
IR$\nu$(Nujol)cm$^{-1}$: 1740, 1670
MS(m/e): 356(M$^+$)
Sodium salt;
m. p. 140°–150° C.
IR$\nu$(Nujol)cm$^{-1}$: 3400, 1660(broad)

EXAMPLE 11

(1) A solution of 12.2 ml of 1.6M n-butyl lithium in hexane is added dropwise to a solution of 2.45 g of 1-ethoxymethyl-pyrazole in 50 ml of tetrahydrofuran at −60° to −50° C. under argon gas atmosphere and the mixture is stirred at the same temperature for 40 minutes. A solution of 5.23 g of lithium 4,5-dichloro-6-formyl-1,3-benzodioxole-2-carboxylate in 40 ml of hexamethylphosphoric triamide is added dropwise to the reaction mixture at −60° to −50° C. and the mixture is stirred at the same temperature for 30 minutes. An aqeous saturated ammonium chloride solution and 1N hydrochloric acid are added to the reaction mixture, and the mixture is extracted with ethyl acetate. An excess amount of a solution of diazomethane in ether is added to the extract (the extract contains 4,5-dichloro-6-[(1-ethoxymethylpyrazol-5-yl)-hydroxymethyl]-1,3-benzodioxole-2-carboxylic acid) and the mixture is stirred for 10 minutes. The mixture is evaporated to remove solvent and the residue is purified by silica gel column chromatography (solvent: chloroform-acetone-ethanol) to give 5.9 g of methyl 4,5-dichloro-6-[(1-ethoxymethyl-pyrazol-5-yl)-hydroxymethyl]-1,3-benzodioxole-2-carboxylate (a mixture of diastereoisomers thereof) as an oil. Yield: 75%

IR$\nu$(liquid)cm$^{-1}$: 3250, 1760
MS(m/e): 402(M$^+$)

(2) 11.0 g of pyridinium dichromate are added to a solution of 5.9 g of methyl 4,5-dichloro-6-[(1-ethoxymethylpyrazol-5-yl)-hydroxymethyl]-1,3-benzodioxole-2-carboxylate in 150 m of methylene chloride and the mixture is stirred at room temperature for 16 hours. The reaction mixture is subjected to silica gel column chromatograhphy (solvent; chloroform-ethyl acetate). The fractions containing the desired compound are collected and evaporated to remove solvent to give 4.61 g of methyl 4,5-dichloro-6-(1-ethoxymethyl-5-pyrazolylcarbonyl)-1,3-benzodioxole-2-carboxylate as an oil. Yield: 78%

IR$\nu$(liquid)cm$^{-1}$: 1755, 1660
MS(m/e): 400(M+)

EXAMPLE 12

(1) The corresponding starting compound is treated in the same manner as described in Example 11-(1) to give methyl 4,5-dichloro-6-[(1-methoxymethyl-pyrazol-5-yl)-hydroxymethyl]-1,3-benzodioxole-2-carboxylate. Yield: 74%

(2) Methyl 4,5-dichloro-6-((1-methoxymethyl-pyrazol-5-yl)-hydroxymethyl)-1,3-benzodioxole-2-carboxylate is treated in the same manner described in Example 11-(2) to give methyl 4,5-dichloro-6-(1-methoxymethyl-5-pyrazolylcarbonyl)-1,3-benzodioxole-2-carboxylate. Yield: 95%

IR$\nu$(liquid)cm$^{-1}$: 1755, 1660
MS(m/e): 386(M+)

EXAMPLE 13

(1) 1.25 ml of 1.6M n-butyl lithium in n-hexane is added dropwise to a solution of 252 mg of 1-ethoxymethyl-pyrazole in 5 ml of tetrahydrofuran at $-60°$ to $-50°$ C. 0.4 ml of hexamethylphosphoric triamide is added to the mixture and the mixture is stirred at the same temperature for 1 hour. The mixture is added to a solution of 582 mg of ethyl 4,5-dichloro-6-formyl-1,3-benzodioxole-2-carboxylate in 10 ml of tetrahydrofuran at $-60°$ to $-50°$ C. and the mixture is stirred at the same temperature for 5 minutes. An aqueous saturated ammonium chloride solution is added to the mixture and the mixture is extracted with ethyl acetate. The extract is washed, dried and evaporated to remove solvent. The residue is purified by silica gel column chromatography (solvent; chloroform-acetone-ethanol) to give 240 mg of ethyl 4,5-dichloro-6-[(1-ethoxymethyl-pyrazol-5-yl)-hydroxymethyl]-1,3-benzodioxole-2-carboxylate.

IR$\nu$(liquid)cm$^{-1}$: 3250, 1760
MS(m/e): 416(M+)

(2) Ethyl 4,5-dichloro-6-((1-ethoxymethyl-pyrazol-5-yl)-hydroxymethyl)-1,3-benzodioxole-2-carboxylate is treated in the same manner described in Example 11-(2) to give ethyl 4,5-dichloro-6-(1-ethoxymethyl-5-pyrazolylcarbonyl)-1,3-benzodioxol-2-carboxylate. Yield: 53%

IR$\nu$(liquid)cm$^{-1}$: 1755, 1660
MS(m/e): 414(M+)

EXAMPLE 14

A mixture of 1.12 g of 1-methoxymethyl-pyrazole, 25 ml of tetrahydrofuran, 6.88 ml of 1.6M n-butyl lithium and a solution of 2.69 g of lithium 4,5-dichloro-6-formyl-1,3-benzodioxole-2-carboxylate in 12 ml of hexamethylphosphoric triamide is treated in the same manner described in Example 11-(1) to give an ethyl acetate solution containing 4,5-dichloro-6-[(1-methoxymethyl-pyrazol-5-yl)hydroxymethyl)-1,3-benzodioxole-2-carboxylic acid. The ethyl acetate solution is washed with water, dried and evaporated to remove solvent under reduced pressure. The residue (crude 4,5-dichloro-6-[(1-methoxymethyl-pyrazol-5-yl)hydroxymethyl]-1,3-benzodioxole-2-carboxylic acid) is dissolved in 100 ml of methylene chloride, 10 g of pyridinium dicromate are added thereto and the mixture is stirred at room temperature for 17 hours. Insoluble materials are filtered off and washed with methylene chloride. The filtrate and the washing solution are combined and evaporated under reduced pressure to remove solvent. Ethyl acetate is added to the residue and insoluble materials are filtered off. The filtrate is washed, dried and evaporated under reduced pressure to remove solvent. The residue is recrystallized from ethyl acetate-n-hexane to give 1.57 g of 4,5-dichloro-6-(1-methoxymethyl-5-pyrazolylcarbonyl)-1,3-benzodioxole-2-carboxylic acid.

m. p. 168°–170° C.
MS(m/e): 372(M+)
IR$\nu$(Nujol)cm$^{-1}$: 1740, 1670, 1480, 1400

EXAMPLE 15

A solution of 1.53 g of sodium bromate trihydrate in 5 ml of water is added to a solution of 2.0 g of ethyl 4,5-dichloro-6-(1-methyl-5-pyrazolylcarbonyl)-1,3-benzodioxole-2-carboxylate in 20 ml of acetic acid at room temperature. The mixture is stirred at the same temperature for 15 hours. The reaction mixture is concentrated under reduced pressure to remove acetic acid. The residue is neutralized by addition of an aqueous saturated sodium bicarbonate solution and extracted with ethyl acetate. The extract is washed with water, dried and evaporated to remove solvent. The residue is purified by silica gel column chromatography (solvent; n-hexane-ethyl acetate) to give 1.0 g of ethyl 4,5-dichloro-6-(1-methyl-4-bromo-5-pyrazolylcarbonyl)-1,3-benzodioxole-2-carboxylate as an oil.

IR$\nu$(liquid)cm$^{-1}$: 1760, 1660
MS(m/e): 448(M+)

EXAMPLE 16

A solution of 0.36 g of sodium hydroxide in 15 ml of water is added to a suspension of 1.86 g of ethyl 4,5-dichloro-6-(1-methyl-5-pyrazolylcarbonyl)-1,3-benzodioxole-2-carboxylate in 35 ml of ethanol and the mixture is stirred at room temperature for 0.5 hour. The reaction mixture is concentrated to remove ethanol and adjusted to pH 1 with aqueous 10% hydrochloric acid. The resultant crystals are collected by filtration, washed successively with water and isopropyl ether and dried to give 1.66 g of 4,5-dichloro-6-(1-methyl-5-pyrazolylcarbonyl)-1,3-benzodioxole-2-carboxylic acid. Yield: 97% m. p. 251.5°–252° C. (decomp.)
IR$\nu$(Nujol)cm$^{-1}$: 1730, 1660
MS(m/e): 342(M+) Sodium salt;
m. p. 190°–195° C. (decomp.)
IR$\nu$(Nujol)cm$^{-1}$: 3400, 1660

EXAMPLES 17–24

The corresponding starting compounds are treated in the same manner as described in Example 16 to give the following compounds as shown in Table 3.

TABLE 3

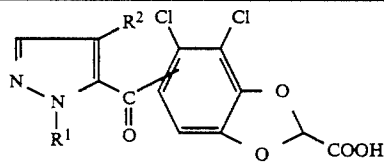

(I-b)

| Example Nos. | Compound (I-b) R¹ | R² | *Position | Properties |
|---|---|---|---|---|
| 17 | CH₃— | H | 7 | Yield: 86%<br>m.p. 259–262° C.<br>IRν(Nujol)cm⁻¹:<br>2440, 1880,<br>1730, 1660, 1620<br>MS(m/e): 342(M⁺) |
| **18 | " | Br | 6 | Yield: 87%<br>m.p. 165° C. (decomp.)<br>IRν(Nujol)cm⁻¹:<br>1750, 1660<br>MS(m/e): 420(M⁺) |
| 19 | CH₃CH₂— | H | " | Yield: 95%<br>m.p. 233–235° C. (decomp.)<br>IRν(Nujol)cm⁻¹:<br>1740, 1670,<br>MS(m/e): 356(M⁺) |
| 20 | CH₃CH₂CH₂— | " | " | Yield: 61%<br>m.p. 179.5–181.5° C.<br>IRν(Nujol)cm⁻¹:<br>2500–2400,<br>1870, 1740, 1670<br>MS(m/e): 370(M⁺) |
| 21 | (CH₃)₂CH— | " | " | Yield: 70%<br>m.p. 212–214.5° C.<br>IRν(Nujol)cm⁻¹:<br>1740, 1640,<br>MS(m/e): 370(M⁺) |
| 22 | CH₃(CH₂)₅— | " | " | Yield: 88%<br>m.p. 119–121° C.<br>IRν(Nujol)cm⁻¹:<br>1740, 1680,<br>MS(m/e): 412(M⁺) |
| 23 | phenyl | " | " | Yield: 88%<br>m.p. 87–90° C.<br>IRν(Nujol)cm⁻¹:<br>1750, 1670,<br>(MS(m/e): 404(M⁺) |
| 24 | CH₃CH₂OCH₂— | " | " | Yield: 96%<br>m.p. 113–115° C.<br>IRν(Nujol)cm⁻¹:<br>2800–2500,<br>1740, 1660, 1670<br>MS(m/e): 386(M⁺) |

Notes:
*Position means the position of the 1-substituted pyrazolyl-5-carbonyl group which is substituted on the benzodioxole skeleton.
**The product of Example 18 was prepared by using potassium hydroxide as a base instead of sodium hydroxide in Example 16.

EXAMPLE 25

1.5 g of ethyl 4,5-dichloro-6-(1-[2-pyridyl]-5-pyrazolylcarbonyl)-1,3-benzodioxole-2-carboxylate are dissolved in a mixture of 18 ml of tetrahydrofuran and 2 ml of water. 177 mg of lithium hydroxide monohydrate are added to the solution and the mixture is stirred at room temperature for one hour. The reaction mixture is concentrated under reduced pressure to remove tetrahydrofuran. Water and 1N hydrochloric acid are added to the residue, and the mixture is extracted with ethyl acetate. The extract is washed with water, dried and evaporated under reduced pressure to remove solvent. The residue is recrystallized from ethyl acetate-n-hexane to give 1.35 g of 4,5-dichloro-6-[1-(2-pyridyl)-5-pyrazolylcarbonyl]-1,3-benzodioxole-2-carboxylic acid.
Yield: 96%
m. p. 211°–214° C. (decomp.)
IRν(Nujol)cm⁻¹: 1740, 1660, 1600
MS(m/e: 370(M⁺-Cl)

EXAMPLES 26–28

The corresponding starting compounds are treated in the same manner as described in Example 25 to give the following compounds as shown in Table 4.

TABLE 4

(I-b)

| Example Nos. | Compound (I-b) R¹ | R² | Properties |
|---|---|---|---|
| 26 | CH₃— | Cl | Yield: 87%<br>IRν(Nujol)cm⁻¹: 1760, 1660,<br>1480, 1220, 1080 |
| 27 | CH₃CH₂OCH₂— | H | Yield: 96%<br>m.p. 113–115° C.<br>IRν(Nujol)cm⁻¹: 2800–2500,<br>1740, 1660, 1670<br>MS(m/e): 386(M⁺) |
| 28 | CH₃OCH₂— | " | Yield: 87%<br>m.p. 168–170° C.<br>IRν(Nujol)cm⁻¹: 1740, 1670,<br>1480, 1400<br>MS(m/e): 372(M⁺) |

Preparation 1

(1) A suspension of 104 g of 3,4-dichloro-1,2-benzenediol, 240 g of potassium carbonate and 354 g of methyl iodide in 2 litters of acetone is refluxed for 2 hours. The reaction mixture is filtered and washed with acetone. The filtrate and the washings are combined and evaporated to remove solvent. Water is added to the residue and the mixture is extracted with ethyl acetate. The extract is washed with water, dried and evaporated to remove solvent. The residue is distilled under reduced pressure to give 110.5 g of 1,2-dichloro-3,4-dimethoxybenzene.
b. p. 103°–105° C. (2 mmHg)

(2) 105.2 g of dichloromethoxymethane are added to a solution of 122.6 g of 1,2-dichloro-3,4-dimethoxybenzene in methylene chloride, and titanium tetrabromide is added dropwise to the mixture at −50° to −60° C. The mixture is stirred at room temperature for 20 hours. The reaction mixture is poured into water and the organic layer is separated. The aqueous layer is extracted with chloroform, and the extract and the above-obtained organic layer are combined. The mixture is washed with water, dried and evaporated to remove solvent. The residue is washed with n-hexane to give 106 g of 2,3-dichloro-4,5-dimethoxybenzaldehyde.
m. p. 120°–123° C.

4.0 g of 3,4-dichloro-5,6-dimethoxybenzaldehyde are obtained from the washings (n-hexane solution).
m. p. 75°–77° C.

(3) 18 ml of 1.6M n-butyl lithium in n-hexane is added dropwise to a solution of 2.26 g of 1-methyl-pyrazole in tetrahydrofuran at −60° C. under argon gas atmosphere and the mixture is stirred at the same temperature for 1 hour. A solution of 5.88 g of 2,3-dichloro-4,5- dimethoxybenzaldehyde in tetrahydrofuran is added dropwise to the mixture at −60° to −50° C. and the mixture is stirred at −50° C. to room temperature for 1 hour. An aqueous ammonium chloride solution is added to the reaction mixture and the mixture is concentarated to remove organic solvent. The residue is extracted with ethyl acetate, and the extract is washed, dried and evaporated to remove solvent. The residue is crystallized from isopropyl ether to give 7.18 g of α-(1-methylpyrazol-5-yl)-2,3-dichloro-4,5-dimethoxybenzylalcohol.

m. p. 149°–154° C.

(4) 20 g of manganese dioxide are added to a solution of 7.08 g of α-(1-methylpyrazol-5-yl)-2,3-dichloro-4,5-dimethoxybenzylalcohol in methylene chloride and the mixture is stirred at room temperature for 3 days. The reaction mixture is filtered and washed with chloroform. The filtrate and the washings are combined and evaporated to remove solvent. The residue is crystallized from n-hexane to give 6.35 g of (1-methylpyrazol-5-yl)-(2,3-dichloro-4,5-dimethoxyphenyl)-methanone.

m. p. 99.5°–101° C.

The corresponding benzylalcohol compounds are treated in the same manner as described above to give the following compounds as shown in Table 5.

TABLE 5

(VI-a)

| Compound (VI-a) $R^1$ | Properties |
|---|---|
| *CH₃— | IR$\nu$(liquid)cm$^{-1}$: 1660 |
| C₂H₅— | m.p. 109–111.5° C. |
| CH₃CH₂CH₂— | m.p. 94–95.5° C. |
| (CH₃)₂CH— | m.p. 103–104° C. |
| CH₃(CH₂)₅— | IR$\nu$(liquid)cm$^{-1}$: 1660 |
| phenyl | m.p. 190–192° C. |
| pyridyl | m.p. 112–115° C. |

Note;
*The chemical name of the compound is (1-methylpyrazol-5-yl)-(3,4(dichloro-5,6-dimethoxyphenyl)methanone.

Preparation 2

(1) A solution of 2.51 g of boron tribromide in methylene chloride is added to dropwise to a solution of 0.47 g of 2,3-dichloro-4,5-dimethoxybenzaldehyde in methylene chloride at −50° to −60° C. and the mixture is stirred at −50° C. to room temperature for 1 hour. The reaction mixture is poured into water and the aqueous mixture is extracted with ethyl acetate. The extract is evaporated to remove solvent. Methanol and 10% hydrochloric acid are added to the residue and the mixture is stirred at room temperature for 1 hour. To the reaction mixture are added water, and the mixture is extracted with ethyl acetate. The extract is washed with water, dried and evaporated to remove solvent. The residue is washed with n-hexane and dried to give 0.38 g of 2,3-dichloro-4,5-dihydroxybenzaldehyde.

m. p. 196°–199° C. (decomp.)

(2) 5 ml of 1.6 M n-butyl lithium in hexane and 1.35 ml of hexamethylphosphoric triamide are added dropwise to a solution of 1.01 g of 1-ethoxymethylpyrazol in tetrahydrofuran at −50° to −60° C. and the mixture is stirred at the same temperature for 1 hour. A solution of 0.5 g of 2,3-dichloro-4,5-dihydroxybenzaldehyde in tetrahydrofuran is added to the mixture at the same temperature and the reaction mixture is stirred at −50° C. to room temperature for 1 hour. An aqueous ammonium chloride solution is added to the reaction mixture and the mixture is extracted with chloroform. The extract is washed with water, dried and evaporated to remove solvent. The residue is dissolved in dimethylformamide, and 0.74 g of potassium carbonate and 1.31 g of ethyl dibromoacetate are added to the solution. The mixture is stirred at 100° C. for 2 hours and evaporated to remove solvent. Ethyl acetate and water are added to the residue and the oragnic layer is separated, washed with water, dried and evaporated to remove solvent. The residue is purified by silica gel column chromatography to give 0.31 g of ethyl 4,5-dichloro-6-[(1-ethoxymethylpyrazol-5-yl)hydroxymethyl]-1,3-benzodioxole-2-carboxylate.

IR$\nu$(liquid)cm$^{-1}$: 3250, 1760

Preparation 3

19.3 g of an aqueous 10% sodium hypochlorite solution are added to a solution of 3.9 g of α-(1-methylpyrazol-5-yl)-2,3-dichloro-4,5-dimethoxybenzylalcohol in acetic acid and the mixture is stirred at room temperature for 2 hours. The reaction mixture is concentrated to remove acetic acid, and ethyl acetate is added to the residue. The organic layer is separated, washed with water, dried and evaporated to remove solvent. The residue is purified by silica gel column chromatography to give 2.1 g of (1-methyl-4-chloropyrazol-5-yl)-(2,3-dichloro-4,5-dimethoxyphenyl)-methanone.

m. p. 118°–120° C.

Preparation 4

(1) A mixture of 11.0 g of 3,4-dichloro-1,2-benzenediol, 15.38 g of potassium carbonate, 27 g of ethyl dibromoacetate and 100 ml of dimethylformamide is stirred at 100° C. under argon gas atmosphere for 4 hours. The reaction mixture is evaporated to remove solvent and ethyl acetate and water is added to the residue. The organic layer is separated, washed with water, dried and evaporated to remove solvent. The residue is purified by silica gel column chromatography to give 10.75 g of ethyl 4,5-dichloro-1,3-benzodioxole-2-carboxylate.

m. p. 58°–61° C.

(2) 3.52 ml of titanium tetrachloride are added dropwise to a mixture of 4.0 g of ethyl 4,5-dichloro-1,3-benzodioxole-2-carboxylate, 2.12 ml of dichloromethoxymethane and 60 ml of methylene chloride at −60° C. and the mixture is stirred at room temperature for 2 days. 2.1 ml of dichloromethoxymethane and 2.1 ml of titanium tetrachloride are added to the reaction mixture at −60° C. and the mixture is stirred at room temperature for 18 hours. The reaction mixture is poured into a mixture of ethyl acetate and an aqueous sodium bicarbonate solution, and the organic layer is separated. The organic layer is washed with water, dried and evaporated to remove solvent. The residue is purified by silica gel column chromatography to give 3.21 g of ethyl 4,5-dichloro-6-formyl-1,3-benzodioxole-2-carboxylate.

m. p. 81°–83° C.

(3) 1.03 g of lithium hydroxide monohydrate are added to a solution of 7.0 g of ethyl 4,5-dichloro-6-formyl-1,3-benzodioxole-2-carboxylate in methanol under ice-cooling and the mixture is stirred at room temperature for 4 hours. Isopropyl ether is added to the reaction mixture and the resultant powdery materials are collected by filtration to give 6.48 g of lithium 4,5-dichloro-6-formyl-1,3-benzodioxole-2-carboxylate.

m. p.>300° C.

What we claim is:

1. A benzodioxole derivative of the formula:

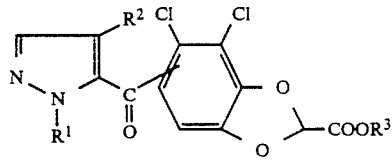

(I)

wherein $R^1$ is a lower alkyl group, $R^2$ is a hydrogen atom and $R^3$ is a hydrogen atom or a salt thereof.

2. The compound according to claim 1, in which $R^1$ is a $C_{1-6}$alkyl group, $R^2$ is a hydrogen atom, and $R^3$ is a hydrogen atom.

3. The compound according to claim 1, in which $R^1$ is a $C_{1-4}$alkyl group, $R^2$ is a hydrogen atom and $R^3$ is a hydrogen atom.

4. The compound according to claim 2, in which $R^1$ is a methyl group, ethyl group, n-propyl group or isopropyl group, $R^2$ is a hydrogen atom, $R^3$ is a hydrogen atom and the 1-substituted 5-pyrazolylcarbonyl group is at the 6-position of the benzodioxole skeleton.

5. The compound according to claim 4, which is 4,5-dichloro-6-(1-methyl-5-pyrazolylcarbonyl)-1,3-benzodioxole-2-carboxylic acid or a salt thereof.

6. The compound according to claim 4, which is 4,5-dichloro-6-(1-ethyl-5-pyrazolylcarbonyl)-1,3-benzodioxole-2-carboxylic acid or a salt thereof.

7. The compound according to claim 4, which is 4,5-dichloro-6-(1-propyl-5-pyrazolylcarbonyl)-1,3-benzodioxole-2-carboxylic acid or a salt thereof.

8. A pharmaceutical composition which comprises a therapeutically effective amount of the compound claimed in claim 1 and pharmaceutically acceptable carrier therefor.

9. A method for treatment of congestive heart failure, edema, hydrops ascites, exudative pleurisy, interstitial nephritis, gout or hyperuricemia in a warm-blooded animal which comprises administering to said warm blooded animal an effective amount of the compound claimed in claim 1.

* * * * *